United States Patent
Freund et al.

(10) Patent No.: US 6,639,673 B1
(45) Date of Patent: Oct. 28, 2003

(54) SURFACE COATING MEASUREMENT INSTRUMENT AND APPARATUS FOR DETERMINATION OF COATING THICKNESS

(75) Inventors: Christopher Hayes Freund, McGraths Hill (AU); Roger Pryce Netterfield, Turramurra (AU); Monty Glass, Ryde (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/550,232

(22) Filed: Apr. 14, 2000

(51) Int. Cl.⁷ ............................................. G01N 21/21
(52) U.S. Cl. ...................... 356/369; 356/630
(58) Field of Search ................... 356/369, 630

(56) References Cited

U.S. PATENT DOCUMENTS

| | | | | |
|---|---|---|---|---|
| 5,311,285 A | * | 5/1994 | Oshige et al. | 356/367 |
| 5,438,415 A | * | 8/1995 | Kazama et al. | 356/367 |
| 5,754,294 A | * | 5/1998 | Jones et al. | 356/432 |
| 5,835,220 A | * | 11/1998 | Kazama et al. | 356/237.2 |

* cited by examiner

*Primary Examiner*—Zandra V. Smith
(74) *Attorney, Agent, or Firm*—Wood, Phillips, Katz, Clark & Mortimer

(57) ABSTRACT

An apparatus (10) and method for measuring the average thickness of a non-uniform coating (110) on a rough surface (40) are disclosed. A source of light (20) of substantially a single wavelength is directed at a coated surface (40) under investigation. The light reflected (5) from the surface (40) is incident on two or more photodetectors (70), which measure the intensities of different polarisation states. A processing means (90) is provided to calculate the average coating thickness from the measured polarisation state intensities.

9 Claims, 5 Drawing Sheets

EDX C SIGNAL AND PSI CHANGE FOR SPRAYED SAMPLES

SURFACE COATING MEASUREMENT INSTRUMENT AND APPARATUS FOR DETERMINATION OF COATING THICKNESS

FIELD OF THE INVENTION

This invention relates to an instrument for measuring properties of a surface coating. It further relates to apparatus, including the instrument, for the determination of average coating thickness. Particularly, but not exclusively, the surface can be a rough moving surface.

BACKGROUND OF THE INVENTION

There are many instances in industry where coatings are applied to surfaces. Some of these coatings are of a protective nature during the manufacturing process, whilst others are to protect or enhance the surfaces in their post-production applications. Other related fields may include printing and film production methods involving, for example, the application of dampening solution to printing drums.

Taking, by way of specific example, the production of aluminium can stock, a coating of oil is required on each side of the aluminium for lubrication. If too little oil is applied to either side there will be excessive friction between the drums and the processed aluminium, resulting in imperfections in the aluminium produced. If an excessive amount of oil is deposited on the aluminium, lubricant is wasted and must be removed prior to further processing.

It is desirable to be able to measure the thickness of the oil coating that is being applied to the aluminium during production to ensure that the optimum amount of lubrication is being applied.

It is known to use a weighing technique to determine the average thickness of the oil coating. The surface is weighed before and after being coated, thus determining the weight of the oil coating. It is then possible to determine the average thickness of the coating using the weight of the oil in conjunction with the density of the oil and the surface area of the material that is being coated.

The current weighing technique is flawed as it can be significantly influenced by the presence of a few oil droplets. If such oil globules are, indeed, present, they may constitute a major part of the oil mass on the surface being examined, particularly when considering thin film coatings. Subsequently, oil droplets make the average thickness unrepresentative of the true surface coating. Furthermore, as the technique requires the sample to be weighed before and after cleaning, it is not practical for real-time monitoring of the coating thickness during application of the coating. The measurement is done offline with, typically, a 1 m² sample taken every several kilometers of strip.

Close examination of the surface of the aluminium can stock has shown that the surface is rough. It has been determined that the oil does not cover the surface evenly; rather, the coating fills the troughs present in the surface of the aluminium stock first, whilst the peaks may remain bare.

It is an object of the present invention to determine at least the thickness of a liquid or solid coating on a surface. This object may be extended to determine the weight of a coating.

SUMMARY OF THE INVENTION

The invention discloses an apparatus for measuring the average thickness of a non-uniform coating on a rough surface, comprising:

a source of light of substantially a single wavelength, which is to be directed at a coated surface being examined;

two or more photodetectors for measuring the intensities of different polarisation states of said light that is reflected from the surface; and processing means for calculating the average coating thickness from said polarisation state intensities.

The invention further discloses an apparatus for measuring average thickness of a non-uniform coating on a rough surface comprising:

a source of light of substantially a single wavelength, which is to be directed at a surface being examined;

a polarising prism beamsplitter arranged to receive a reflected beam from said surface and produce an orthogonal pair of reflection components at ±45° to the plane of incidence of said light source;

a pair of photodetectors each receiving a respective one of said reflection components and producing respective intensity signals thereof; and processing means for calculating the average coating thickness from said polarisation state intensities.

The invention yet further discloses a surface coating measurement instrument comprising:

a housing, within which is arranged:
  (a) a light source of substantially a single wavelength, which is to be directed at a coated surface being examined;
  (b) a transmission aperture from which said light emanates;
  (c) a reflection reception aperture through which reflected light passes;
  (d) a polarising prism beamsplitter receiving said reflected light and arranged to produce an orthogonal pair of reflection components at ±45° to the plane of incidence of said light; and
  (e) a pair of photodetectors for measuring the intensities of the different polarisation states from the beamsplitter.

The invention yet further discloses a method for measuring the average thickness of a non-uniform coating on a rough surface, the method comprising the steps of:

directing the beam of light of a substantially single wavelength at a coated surface being examined, said beam being at non-normal incidence to the surface;

measuring the intensities of the different polarisation states of the beam reflected from the said surface coating, using a plurality of photodetectors; and determining the average thickness of the non-uniform coating from the polarisation state intensities.

The invention yet further provides a method for measuring the average thickness of a non-uniform coating on a rough surface, the method comprising the steps of:

directing the source of light of a substantially single wavelength at a coated surface being examined, said beam being at non-normal incidence to the surface;

measuring the intensities of polarisation states of said light for ±45° components to the plane of incidence of said light source; and determining the average thickness of the non-uniform coating from the polarisation state intensities.

The invention can be practised on moving or static rough surfaces alike. For a static surface, if the instrument or sample is scanned it is possible to form a surface mapping of film thickness.

BRIEF DESCRIPTION OF THE DRAWINGS

Embodiments of the invention will now be described with reference to the accompanying drawings, wherein.

DETAILED DESCRIPTION OF PREFERRED EMBODIMENTS

Figure 1:
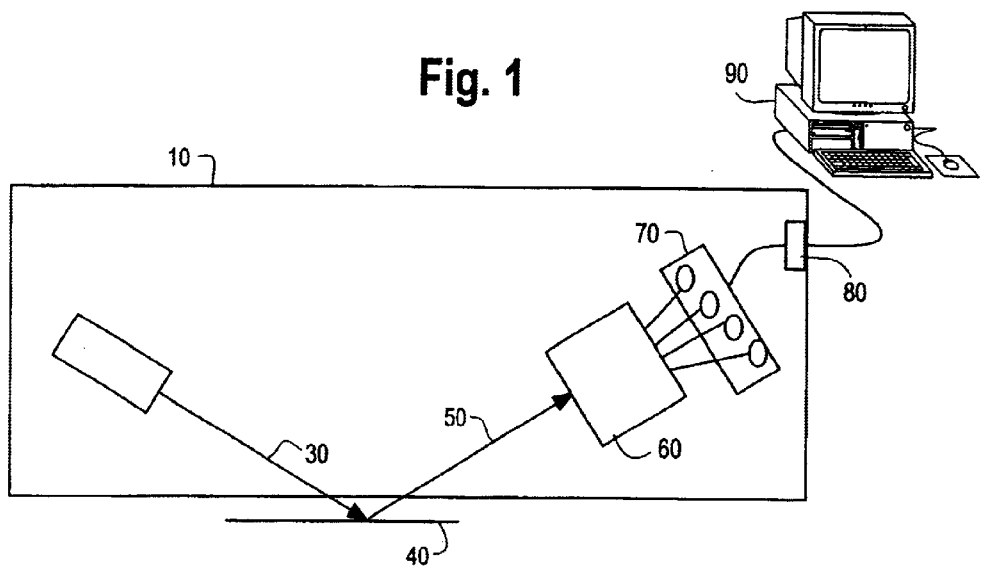
FIG. 1 shows the arrangement of a coating thickness measurement apparatus relative to a surface.

FIG. 1 shows a measurement instrument 10. The instrument has a source of collimated light, in the form of a laser 20, which directs an incident beam of light 30 at a surface 40 having a form of coating. The direct path of reflected light 50 is then intercepted by a beam splitter 60, which splits the light into divergent beams, such that each is incident on one of four polarisation state detectors 70. The polarisation state detectors 70 are connected to an electrical interface 80 which is then connected to an external processor 90, that utilises the electrical signals for the determination of the coating thickness.

Figure 2:
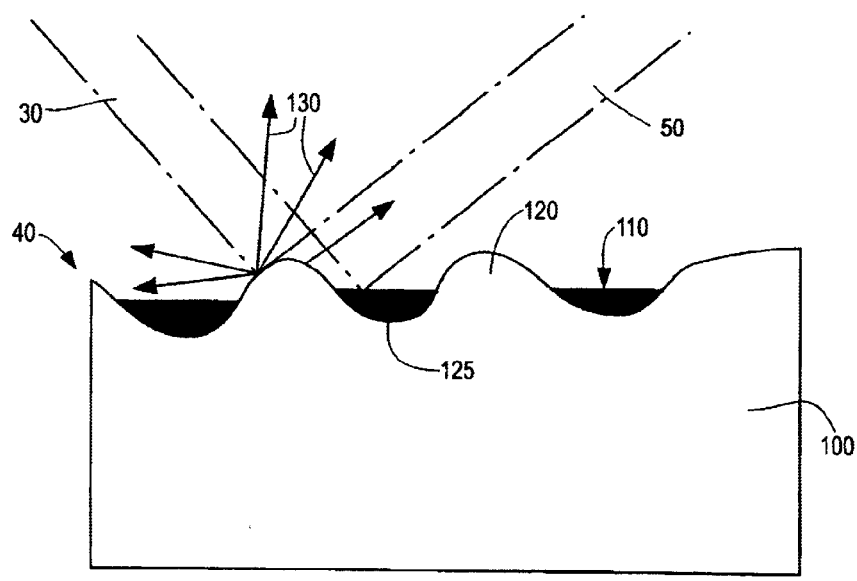
FIG. 2 shows a rough surface having a non-uniform liquid coating.

FIG. 2 shows the incident beam 30, directed at a non-normal angle, at the point of incidence with the surface 40 of a representative substrate 100. The surface is rough and has a non-uniform liquid coating 110. In fact, it is possible that the roughness of the surface may result in the peaks 120 of the substrate not being coated. When the incident beam 30 comes in contact with the coating 110, the exposed peaks 120 and coated roughs 125, it gives rise to many rays of scattered light 130. However, the majority of the incident beam 30 reflected at the liquid surface forms the direct reflected path 50.

Figure 3A:
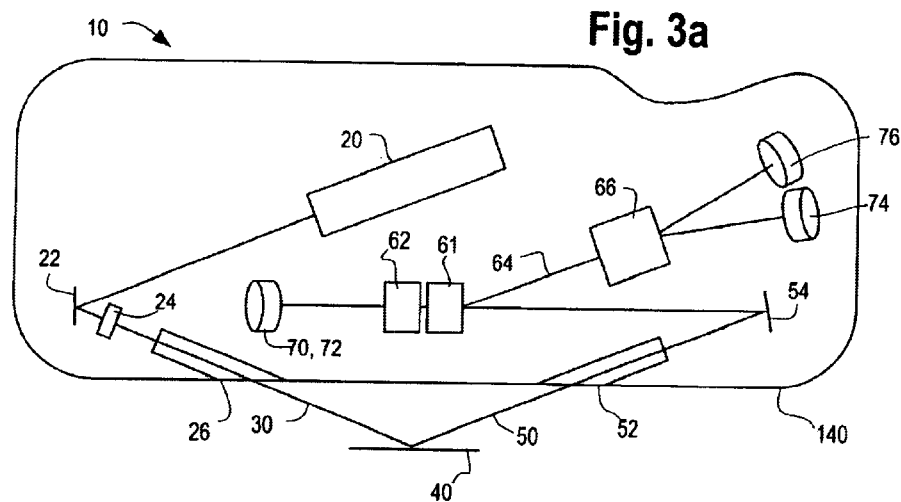
FIGS. 3a to 3c show assembly diagrams of the apparatus of FIG. 1.
Figure 3B:
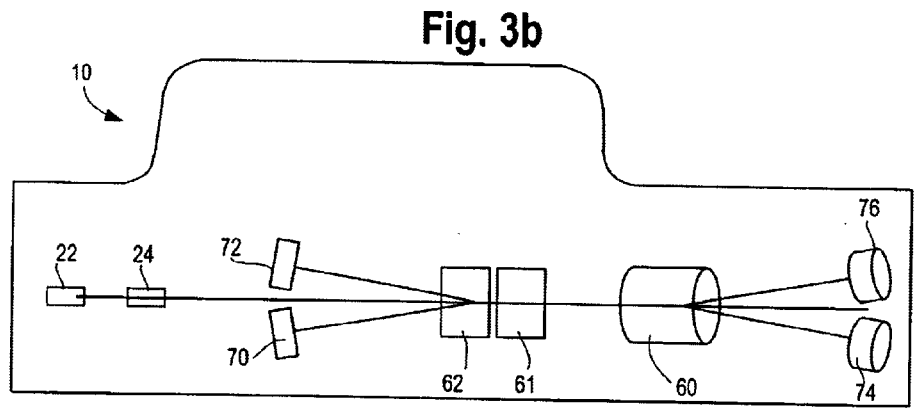
Figure 3C:
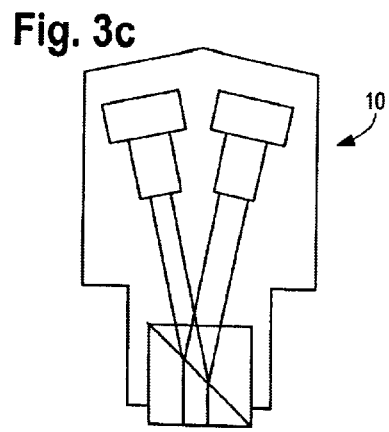

FIGS. 3a to 3c show the constituent components of the instrument 10, located within a housing 140, in more detail. FIG. 3a is a front elevational view, FIG. 3b is a perspective view and FIG. 3c is a partial end elevational view of the instrument. A laser 20 is the source of 670 nm monochromatic light, which is directed at a mirror 22 and is then reflected through a polariser 24. Passing through an air window 26, the incident beam 30 is then directed at a non-normal incidence to the surface 40, which is the subject of investigation. The majority of the incident beam 30 is reflected from the surface 40 and forms the direct path of reflected light 50, which propagates through an air window 52 towards a mirror 54. On reflection from the mirror 54, the beam of light is then incident on a beamsplitter 61, then a Wollaston prism beamsplitter 62. Some of the light passes through the prism 62 and is refracted into divergent paths of light. These divergent paths of light are then incident on two polarisation detectors 70, 72. The remainder of the light incident on the beamsplitter 61 is reflected, and is directed in a path 64 towards a second Wollaston prism beamsplitter 66. Once again the light is refracted into divergent paths, which are incident on two polarisation detectors 74, 76.

The specifications for the components of the instrument 10 are:

| | |
|---|---|
| diode laser 20 | 670 nm |
| polariser 24 | linear, visible |
| polarising prisms 62 | Wollaston 10 deg. sep. |
| detectors 70–76 | Photop Series UDT-020D |

The detectors are connected to an external electrical interface, an A-to-D converter 80 (shown in FIG. 1) and thence to the off-line processor 90.

The instrument 10 measures the change in state of polarised light produced by reflection of light from the can stock. The photodetectors 70, 72, 74, 76 are employed to measure the intensities of different polarisation states of the reflected beam. Each of four photodetectors measures the intensity of light for a different polarisation state resulting from the beamsplitting. The light passing through the first Wollaston prism 62 is split into polarisation states corresponding to the plane of incidence and its respective orthogonal component. The second Wollaston prism 66 is angularly displaced from the first prism 62 such that the orthogonal polarisation states, which have a bearing of ±45° from the plane of incidence, may be examined.

Using a known convention described in R. M. A. Azzam and N. M. Bashara, "Ellipsometry and Polarized Light" p. 174, North-Holland, 1977, the change in the state of polarisation, $\rho$, is written in terms of $\psi$ and $\Delta$ as:

$$\rho = \tan \psi \, \exp(i\Delta)$$

If the detector outputs are assigned as D1, D2, D3 and D4 (corresponding to detectors 70, 72, 74 and 76, respectively), and represent the polarisations with respect to the plane of incidence at 90°, 0°, −45°, and 45° respectively, then:

$$\psi = \arctan\left(\frac{D2}{D1}\right)^{1/2} \quad (1)$$

and $$\Delta = \arccos\left(\frac{(1+\tan^2\psi)\left(1-\frac{D3}{D4}\right)}{2\tan\psi\left(1+\frac{D3}{D4}\right)} - \right) \quad (2)$$

Note that the measures $\psi$ and $\Delta$ are functions only of two polarisation states. Either one or both of $\psi$ and $\Delta$ can be utilised in determining thickness.

As described in Equations 1 and 2, the ratio of intensities of light measured for the plane of incidence and its corresponding normal component allows a variable $\psi$ to be readily derived, which is a measure of the relative amplitude of the reflected light. The corresponding ratio for the intensities of light at ±45° to the plane of incidence, when combined with the newly derived $\psi$, allows $\Delta$ to be ascertained, giving the change in the relative phase of the reflected light.

A further parameter, defined here as $\omega$, can be derived from the ratio of the intensities at ±45° to the plane of incidence, without a knowledge of the quantity $\psi$.

$$\omega = 2\arctan\left(\frac{D3}{D4}\right)^{1/2} \quad (3)$$

Calibration

In order to determine characteristics of the surface coating, it is further necessary to determine reference characteristics of the surface itself. Measurements are performed to derive ω for a clean strip of the material being used. For aluminium can stock, it has been determined that ω was fairly constant for a roller with a given surface finish.

The following process can be followed. Clean Al can stock is sprayed with varying qualities of coating material. Once again, ω is determined using the instrument 10. Furthermore, each sample is examined using an electron microscope equipped with an Energy Dispersive X-ray system capable of measuring the C:Al concentration, which, to a first approximation, is proportional to the thickness of the coating. It was determined that a linear relationship existed between the change in ω between uncoated and coated Al stock. This gives a "slope factor".

In the absence of any droplets of oil, the final calibration step involves weighing a sample of Al can stock with and without a surface coating, and comparing the average weight per area of oil with the change in ω to the get the absolute weight per unit area.

A 'zero offset' for bare Al can also be determined by the abovementioned calibration process.

In an alternative arrangement, ω may change non-linearly in response to changes in thickness of a coating under investigation. Furthermore, the response may be non-monotonic, resulting in two or more possible values for the coating thickness for any given value of ω or ψ. The calibration process may involve the recording of the response of ω and/or ψ to changes in thickness of the coating and then storing the response/s as look-up tables.

Measurements of Thickness

The average thickness of a non-uniform coating can be readily determined by determining ω, subtracting the zero offset and multiplying by a slope factor. The processor 90 is appropriately programmed to store the zero offset and slope factor, and to receive the digital polarization signals from the A-to-D Convertor 80 and, in real time, calculate average thickness by applying the above-noted technique on repeated measurements at a single point, or from multiple measurements across a surface.

Whilst the foregoing discussion has focussed on use of ω to determine thickness, it is equally possible to use ψ (thickness again being (ψ-offset) x slope factor), although ψ may exhibit lesser sensitivity than ω.

There may be instances—depending upon the nature of the surface coating material—where it would be desirable to utilise both ω and ψ, or both Δ and ψ. If ω and ψ vary monotonically with respect to the thickness of the coating under investigation, it may be sufficient to use just one of ω or ψ, irrespective of whether the response is linear or non-linear. If, however, ω and ψ vary non-monotonically with respect to the thickness of the coating being investigated, it is insufficient to use only one of ω and ψ.

A non-monotonic function may give two possible coating thickness values for any given value of ω or ψ. Look-up tables generated during the calibration process may be used to compare the two possible values for the coating thickness generated by each of ω and ψ, or Δ and ψ. The possible value for the coating thickness that matches for each of ω and ψ, or Δ and ψ, is the correct value of the coating thickness.

Figure 7A:
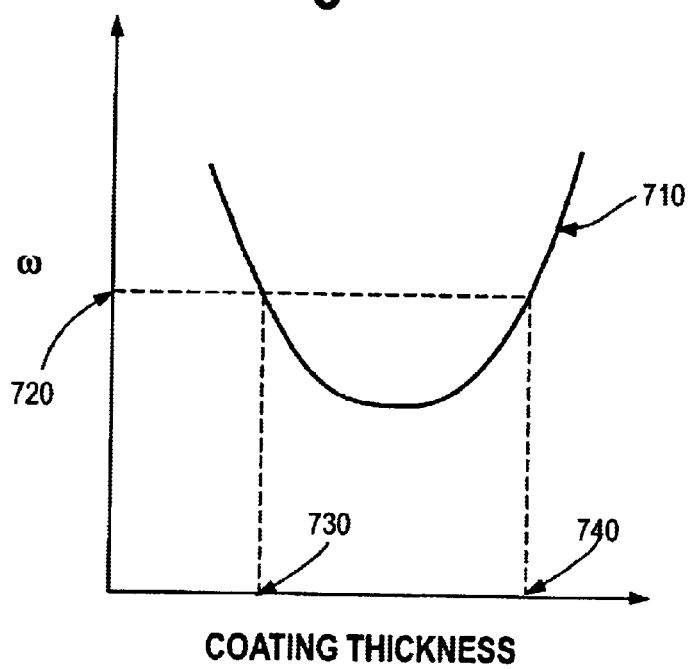
FIGS. 7A and 7B are plots of non-linear, non-monotonic responses of $\omega$ and $\psi$ to changes in a coating thickness.
Figure 7B:
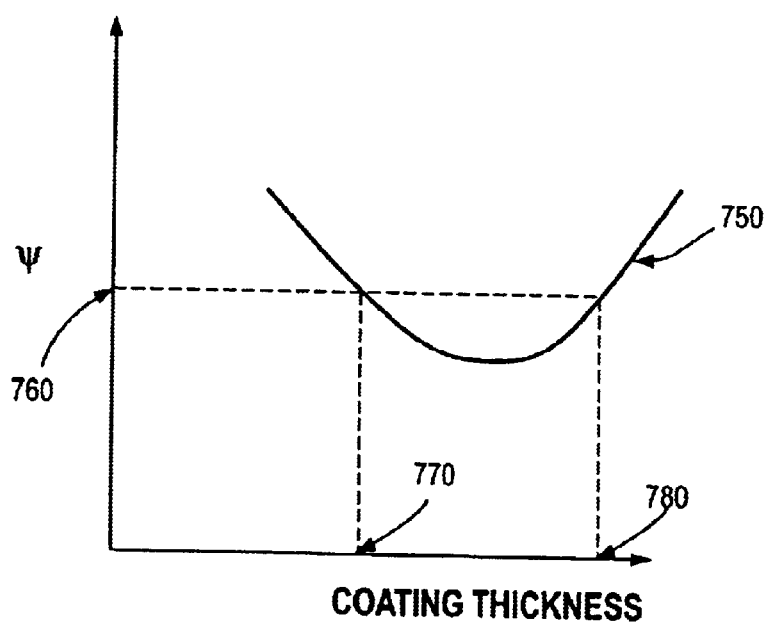

FIG. 7A shows a non-linear, non-monotonic response 710 of ω to changes in a coating thickness. A given value 720 of ω has two possible values 730, 740 for the coating thickness. FIG. 7B shows a non-linear, non-monotonic response 750 of ψ to changes in thickness of the coating of FIG. 7A. A given value 760 of ψ has two possible values 770, 780 for the coating thickness. It is not possible to determine which of the values 730 and 740, and 770 and 780, generated by each of ω and ψ, respectively, is correct by using only one of ω or ψ. By using both ω and ψ, however, it is possible to determine which of the possible coating thickness values 730, 740, 770 and 780 match. The matching values indicate the correct coating thickness.

The choice of wavelength of the source light from the laser can also be considered as a variable that is a function of the coating material. For example, for a coating of a waxy substance, wavelengths below 670 nm may be more suitable from the point of view of sensitivity. The choice of wavelength of light for particular coatings is to be determined empirically.

Specific Example

Figure 4:
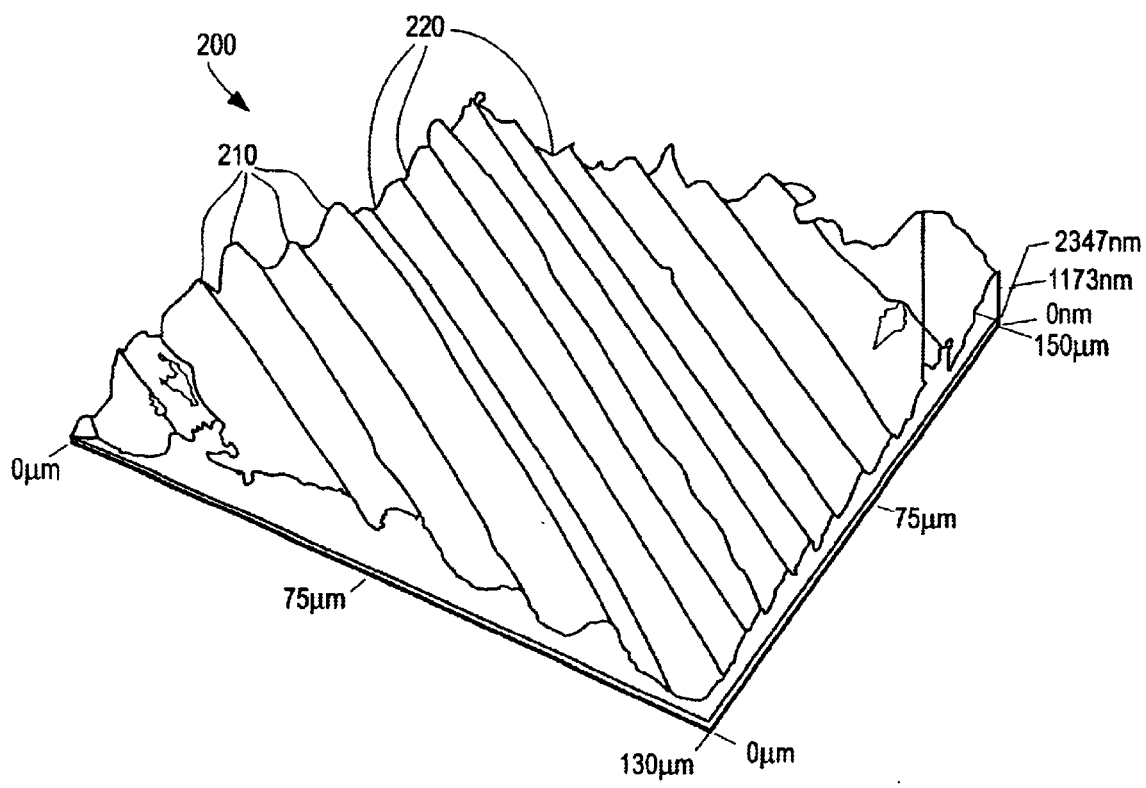
FIG. 4 shows a specimen surface of aluminium can stock.

FIG. 4 shows a specimen surface of aluminium can stock 200 obtained by atomic force microscopy (AFM). It is clearly evident that the surface is not smooth, and is in fact made up of a number of peaks 210 and troughs 220.

For a sample of aluminium can stock of the nature shown in FIG. 4, moving at a line speed of 8 m/s, the detection instrument 10 and a personal computer 90 were used to determine the moving average thickness of the oil film coating.

Figure 5:
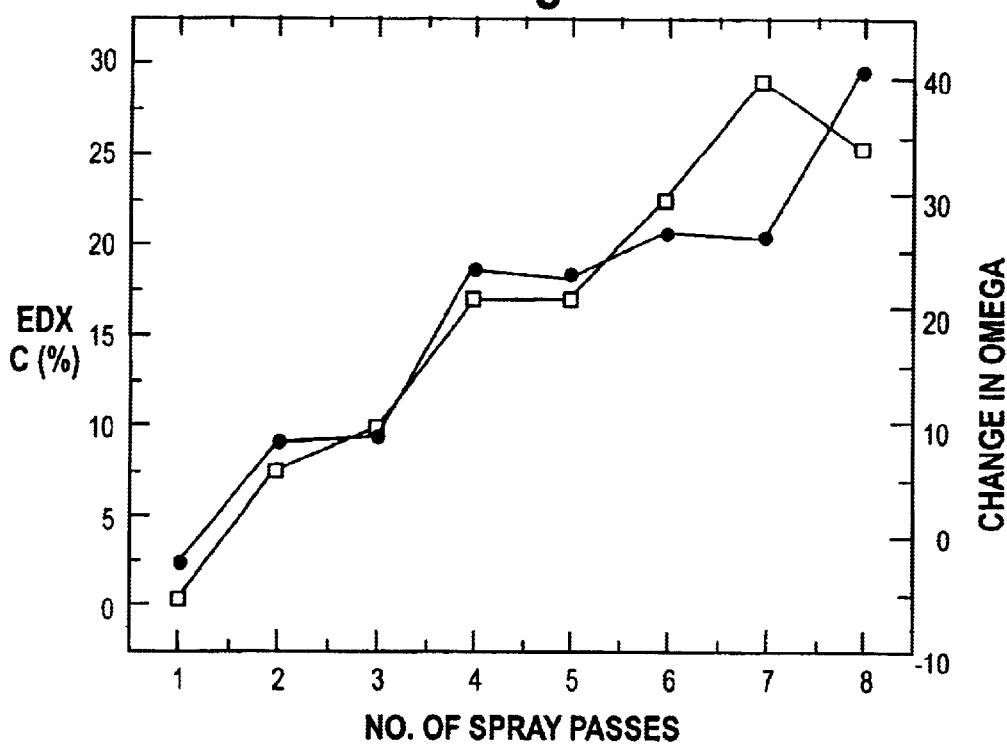
FIG. 5 is a plot of thickness and $\omega$ against thickness of coating.

FIG. 5 shows experimental results where the aluminium can stock surface was sprayed with a coating of oil in a number of discrete passes, represented by the x-axis. Plotted on the left-hand y-axis is the percentage of $C_{12}$, determined by the aforementioned Energy Dispersive X-ray technique, the data for which is represented by the points indicated as squares. The right-hand y-axis is in units of the change of ω, the data for which is indicated as circles. Both measures of thickness indicate an approximately linear relation with thickness of coating, and also have reasonably good agreement.

Figure 6:
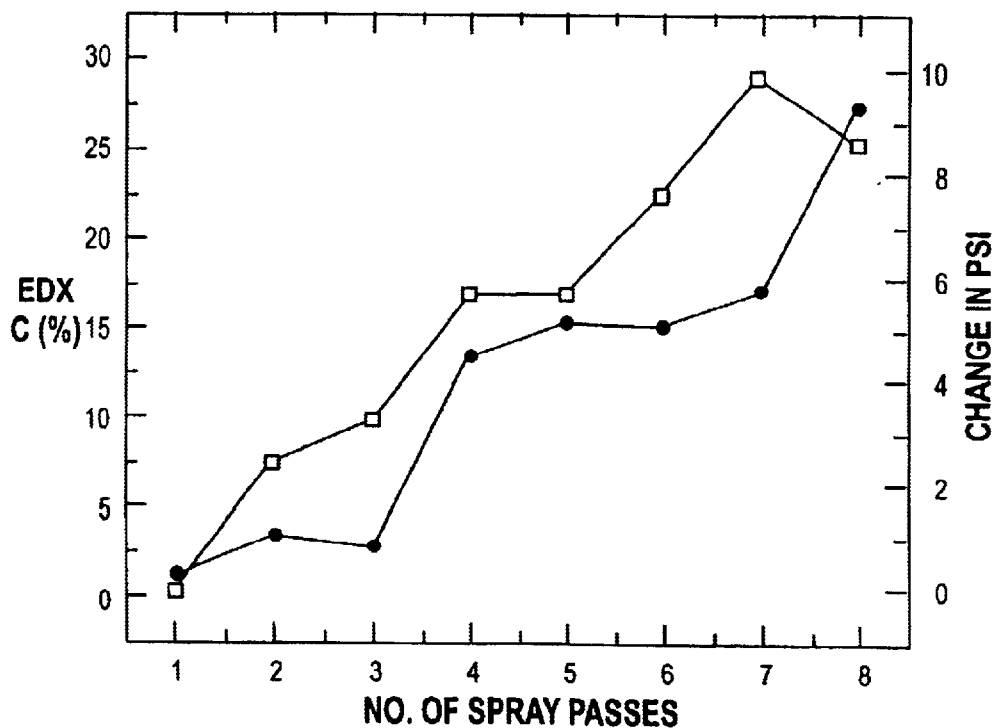
FIG. 6 is a plot of thickness of $\psi$ against thickness of coating.

FIG. 6 is a similar plot of experimental results, except that the right-hand y-axis indicates a change in ψ, suggesting a slightly less linear relation with thickness of coating, but otherwise reasonable correspondence with the weight determination.

The invention can be practised on many different surface-coating materials. One other specific embodiment measures the average surface thickness of thin wax or zirconium dioxide ($ZrO_2$) for thicknesses of $\leq 1$ μm.

The foregoing describes only some embodiments of the present invention, and modifications and/or changes can be made thereto without departing from the scope and spirit of the invention, the embodiments being illustrative and not restrictive.

We claim:

1. Apparatus for measuring the average thickness of a non-uniform coating on a rough surface, comprising:
    a source of light of substantially a single wavelength, which is to be directed at a coated surface being examined;
    at least one polarising beam splitter receiving light reflected from said coated surface to produce a pair of orthogonal reflection components at 0° and 90° to the plane of incidence of said light source;
    at least two photodetectors for measuring the intensities, D1 for 0° and D2 for 90° of said orthogonal reflection components; and processing means coupled to the photodetectors that determines a variable $\psi$ by the calculation:

$$\psi = \arctan\left(\frac{D2}{D1}\right)^{1/2}$$

and subtracts a predetermined zero offset from $\psi$ and multiplies the result by a predetermined slope factor to give a measure of average thickness of said coating.

2. Apparatus for measuring the average thickness of a non-uniform coating on a rough surface, comprising:
- a source of light of substantially a single wavelength, which is to be directed at a coated surface being examined;
- at least one polarising prism beamsplitter receiving light reflected from said coated surface to produce a pair of orthogonal reflection components at ±45° to the plane of incidence of said light source;
- at least two photodetectors for measuring the intensities, D3 for +45° and D4 for −45° of said orthogonal reflection components; and
- processing means coupled to the photodetectors that determines a variable $\omega$ by the calculation:

$$\omega = 2\arctan\left(\frac{D3}{D4}\right)^{1/2}$$

and subtracts a predetermined zero offset from $\omega$ and multiplies the result by a predetermined slope factor to give a measure of average thickness of said coating.

3. Apparatus for measuring the average thickness of a non-uniform coating on a rough surface, comprising:
- a source of light of substantially a single wavelength which is to be directed at a coated surface to be examined;
- a first polarising beam splitter receiving light reflected from said coated surface to produce a first pair of orthogonal components at 0° and 90° to the plane of incidence of said light source;
- a second polarising beam splitter receiving light reflected from said coated surface to produce a second pair of orthogonal components at ±45° to the plane of incidence of said light source;
- at least four photodetectors for measuring the intensities, D1 for 0°, D2 for 90°, D3 for +45° and D4 for −45°, of said first and second pairs of orthogonal reflection components; and
- processing means that:
  (a) determines a variable $\psi$ by the calculation $$\psi = \arctan\left(\frac{D2}{D1}\right)^{1/2};$$

(b) determines a variable $\omega$ by the calculation $$\omega = 2\arctan\left(\frac{D3}{D4}\right)^{1/2};$$

(c) determines possible thickness values for each of $\psi(T_{\psi_n})$ and $\omega(T_{\omega_n})$ from predetermined tabulated values, wherein $T_{\psi_n}$ and $T_{\omega_n}$ are thickness values; and
  (d) determines the average thickness of said coating for the values of $T_{\psi_n}$ and $T_{\omega_n}$ that substantially match.

4. A computer program, storable in and executable by a computer to determine the average thickness of a non-uniform coating on a rough surface comprising:
- instructions for digitizing a plurality of electrical signals indicative of respective 0° and 90° intensities (D1, D2 respetively) of polarization states of a beam of light of substantially a single wavelength reflected off a location or a sample, said intensities being with reference to the plane of incidence of said beam;
- instructions for determining a variable $\psi$ by performing the calculation $$\psi = \arctan\left(\frac{D2}{D1}\right)^{1/2}; \text{ and}$$

- instructions for subtracting a predetermined zero offset from $\psi$ and multiplying the result by a predetermined slope factor to give a measure of thickness of said coating.

5. A computer program, storable in and executable by a computer to determine the average thickness of a non-uniform coating on a rough surface comprising:
- instructions for digitizing a plurality of electrical signals indicative of respective +45° and −45° intensities (D3, D4 respectively) of polarization states of a beam of light substantially a single wavelength reflected off a location or a sample, said intensities being with reference to the plane of incidence of said beam;
- instructions for determining a variable $\omega$ by performing the calculation $$\omega = 2\arctan\left(\frac{D3}{D4}\right)^{1/2}; \text{ and}$$

- instructions for subtracting a predetermined zero offset from $\omega$ and multiplying the result by a predetermined slope factor to give a measure of thickness of said coating.

6. A computer program, storable in and executable by a computer to determine the average thickness of a non-uniform coating on a rough surface comprising:
- instructions for digitizing a plurality of electrical signals indicative of respective 0°, 90° +45° and −45° (D1, D2, D3, D4 respectively) of polarization states of a beam of light of substantially a single wavelength reflected off a location or a sample, said intensities being with reference to the plane of incidence of said beam;
- instructions for determining a variable $\psi$ by performing the calculation $$\psi = \arctan\left(\frac{D2}{D1}\right)^{1/2};$$

- instructions for determining a variably $\omega$ by performing the calculation $$\omega = 2\arctan\left(\frac{D3}{D4}\right)^{1/2};$$

- instructions for determining possible thickness values for each of $\psi(T_{\psi_n})$ and $\omega(T_{\omega_n})$ from predetermined tabulated values, wherein $T_{\psi_n}$ and $T_{\omega_n}$ are thickness values; and instructions for determining the average thickness of said coating for the values of $T_{\psi_n}$ and $T_{\omega_n}$ that substantially match.

7. A method for measuring the average thickness of a non-uniform coating on a rough surface, comprising the steps of:

performing a calibration operation on a non-coated sample of said rough surface to derive an offset value;

performing a calibration operation to determine a slope factor representing the variation of thickness with a reflectance measure;

directing a source of light of substantially a single wavelength at a coated surface being examined;

causing reflected light components to be split into a pair of orthogonal reflection components at 0° and 90° to the plane of incidence of said light source;

measuring the intensities D1 for 0° and D2 for 90° of said orthogonal reflection components;

determining a variable $\psi$ by the calculation:

$$\psi = \arctan\left(\frac{D2}{D1}\right)^{1/2}; \text{ and}$$

calculating a measure of average thickness of said coating by subtracting said zero value from $\psi$ and multiplying the result by said slope factor.

8. A method for measuring the average thickness of a non-uniform coating on a rough surface, comprising the steps of:

performing a calibration operation on a non-coated sample of said rough surface to derive an offset value;

performing a calibration operation to determine a slope factor representing the variation of thickness with a reflectance measure;

directing a source of light of substantially a single wavelength at a coated surface being examined;

causing reflected light components to be split into a pair of orthogonal reflection components at ±45° to the plane of incidence of said light source;

measuring the intensities D3 for ±45° and D4 for −45° of said orthogonal reflection components;

determining a variable $\omega$ by the calculation:

$$\omega = 2\arctan\left(\frac{D3}{D4}\right)^{1/2} \text{ and;}$$

calculating a measure of average thickness of said coating by subtracting said zero value from $\omega$ and multiplying the result by said slope factor.

9. A method for measuring the average thickness of a non-uniform coating on a rough surface, comprising the steps of:

(a) performing a calibration operation by:
(i) directing a source of light of substantially a single wavelength at a coated sample of said rough surface having a known thickness of coating;
(ii) causing reflected light components to be split into pairs of orthogonal reflection components at 0°, 90°, +45° and −45° to the plane of incidence of said light source;
(iii) measuring the intensities D1 for 0°, D2 for 90°, D3 for +45° and D4 for −45° of said orthogonal components;
(iv) determination a variable $\psi$ by the calculation:

$$\psi = \arctan\left(\frac{D2}{D1}\right)^{1/2};$$

(v) determining a variable $\omega$ by the calculation:

$$\omega = 2\arctan\left(\frac{D3}{D4}\right)^{1/2}; \text{ and}$$

(vi) repeating steps (i) to (v) for a range of known thicknesses of coating and tabulating said respective values of $\psi$ and $\omega$;

(b) performing steps (i) to (v) but for a coated sample of unknown thickness;

(c) determining possible thickness values for each of $\psi(T_{\psi_n})$ and $\omega(T_{\omega_n})$ from said tabulated values, wherein $T_{\psi_n}$ and $T_{\omega_n}$ are thickness values; and (d) determining the average thickness of said coating for the values of $T_{\psi_n}$ and $T_{\omega_n}$ that substantially match.

* * * * *